US009682065B2

(12) United States Patent
Kanaji et al.

(10) Patent No.: US 9,682,065 B2
(45) Date of Patent: Jun. 20, 2017

(54) LEFT VENTRICULAR DIASTOLIC FUNCTION IMPROVING AGENT

(75) Inventors: Toshiya Kanaji, Osaka (JP); Kazuhiro Fuchibe, Osaka (JP); Masaya Takahashi, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 283 days.

(21) Appl. No.: 14/236,474

(22) PCT Filed: Aug. 1, 2012

(86) PCT No.: PCT/JP2012/069609
§ 371 (c)(1),
(2), (4) Date: Jan. 31, 2014

(87) PCT Pub. No.: WO2013/018837
PCT Pub. Date: Feb. 7, 2013

(65) Prior Publication Data
US 2014/0179606 A1 Jun. 26, 2014

(30) Foreign Application Priority Data

Aug. 2, 2011 (JP) ................................ 2011-169389

(51) Int. Cl.
*A61K 31/4015* (2006.01)
*A61K 9/00* (2006.01)
*A61K 9/20* (2006.01)
*C07D 207/26* (2006.01)
*A61K 45/06* (2006.01)

(52) U.S. Cl.
CPC ........ *A61K 31/4015* (2013.01); *A61K 9/0019* (2013.01); *A61K 9/2054* (2013.01); *A61K 45/06* (2013.01); *C07D 207/26* (2013.01)

(58) Field of Classification Search
None
See application file for complete search history.

(56) References Cited

U.S. PATENT DOCUMENTS

| 6,610,719 B2 * | 8/2003 | Paralkar ................. A61K 31/00 514/352 |
| 6,849,657 B2 | 2/2005 | Elworthy et al. |
| 7,608,637 B2 * | 10/2009 | Maruyama ........... A61K 9/0019 514/424 |
| 2001/0041729 A1 | 11/2001 | Paralkar et al. |
| 2003/0064964 A1 | 4/2003 | Elworthy et al. |
| 2005/0020686 A1 | 1/2005 | Maruyama et al. |
| 2008/0021021 A1 | 1/2008 | Okada et al. |
| 2008/0234337 A1 | 9/2008 | Kuwahara et al. |
| 2010/0010222 A1 | 1/2010 | Maruyama et al. |
| 2012/0202773 A1 | 8/2012 | Maruyama et al. |

FOREIGN PATENT DOCUMENTS

| EP | 1 132 086 B1 | 5/2006 |
| EP | 1 782 829 A1 | 5/2007 |
| EP | 1 782 830 A1 | 5/2007 |
| EP | 1 417 975 B1 | 3/2011 |
| JP | 2001-233792 A | 8/2001 |
| JP | 2006321737 A | 11/2006 |
| WO | 03/008377 A1 | 1/2003 |
| WO | 03009872 A1 | 2/2003 |
| WO | 2006016689 A1 | 2/2006 |
| WO | 2006016695 A1 | 2/2006 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002.*
Lam, C. S., Roger, V. L., Rodeheffer, R. J., Borlaug, B. A., Enders, F. T., & Redfield, M. M. (2009). Pulmonary hypertension in heart failure with preserved ejection fraction: a community-based study. Journal of the American College of Cardiology, 53(13), 1119-1126.*
Gheeraert, P. J., De Buyzere, M. L., Taeymans, Y. M., Gillebert, T. C., Henriques, J. P., De Backer, G., & De Bacquer, D. (2006). Risk factors for primary ventricular fibrillation during acute myocardial infarction: a systematic review and meta-analysis. European heart journal, 27(21), 2499-2510.*
Vincent, J. L. (2008). Understanding cardiac output. Critical Care, 12(4), 1.*
Search Report, Issued by the European Patent Office, Dated Jan. 27, 2015, In counterpart European Application No. 12819579.9.
Communication issued by the European Patent Office, dated Nov. 20, 2015, in counterpart European Application No. 12819579.9.
Communication from the State Intellectual Property Office of P.R. China dated Nov. 4, 2015, in counterpart Chinese application No. 201280038310.1.
Communication from the State Intellectual Property Office of P.R. China dated Dec. 15, 2014 in a counterpart application No. 201280038310.1.
Office Action dated Mar. 23, 2015 issued by the Intellectual Property Office of Singapore in counterpart Singapore Patent Application No. 2014007603.

(Continued)

*Primary Examiner* — Shaojia Anna Jiang
*Assistant Examiner* — Dale R Miller
(74) *Attorney, Agent, or Firm* — Sughrue Mion, PLLC

(57) ABSTRACT

An agent for treating heart failure, which improves left ventricular diastolic function itself without depending on the diuretic effect or vasodilation effect; controls the pathological condition of diastolic functional failure; and prevents the recurrence, and can prevent dyspnea and death from the pathological condition, is provided.
By directly acting on a heart, 4-[(2-{(2R)-2-[(1E,3S)-4-(4-fluorophenyl)-3-hydroxy-1-buten-1-yl]-5-oxo-1-pyrrolidinyl}ethyl)thio]butanoic acid improves left ventricular diastolic function, and can effectively treat diastolic functional failure among heart failure types. Accordingly, by present invention, a new agent for treating heart failure that can relieve diastolic functional failure, for which no effective therapeutic method has been established, can be provided.

26 Claims, 3 Drawing Sheets

(56) References Cited

OTHER PUBLICATIONS

Pamela Harding et al.; "Gene expression profiling of dilated cardiomyopathy in older male Ep4 knockout mice"; American Journal of Physiology; Heart and Circulatory Physiology; vol. 298; No. 2; Dec. 11, 2009; 17 pages total.
Segi, Eri; "A study for Functions of Prostaglandin E Receptor EP4 Subtype by Analysing Knockout Mice"; Journal of the Pharmaceutical Society of Japan; vol. 121 No. 1; 2001; eleven (11) pages total.
ISR (PCT/ISA/210) issued Aug. 28, 2012; for corresponding PCT Application No. PCT/JP2012/069609.
Office Action issued on Jun. 1, 2016, by the Australian Patent Office in counterpart Australian Application No. 2012290987.
Communication dated Jan. 19, 2016, issued by the Intellectual Property Office of Taiwan in corresponding Taiwanese Patent Application No. 101127773.
Communication dated Feb. 17, 2016 issued by the Russian Patent Office in counterpart Russian Patent Application No. 2014107904/15.
Communication dated May 30, 2016 issued by the Japanese Patent Office in counterpart Japanese Patent Application No. 2013-526948.
Minushkina L.O. et al.; "Whether valsartan will be first-line agent for treating heart failure"; Pharmateka No. 8; (86); 2004; 16 pgs. total.
M. Woodley et al; "Washington University Therapeutic Guide"; Practice 1995; pp. 129, 156, 157, 179, 238, 244, 247; 22 pgs. total.
A.S. Smetnev et al; "International Diseases"; Medicine 1981; pp. 142, 180, 181; 12 pgs. total.
Communication from the State Intellectual Property Office of P.R. China dated Jun. 10, 2015 in a counterpart Chinese application No. 201280038310.1.
Office Action, dated Aug. 24, 2016, issued in European Patent Application No. 12819579.9.
Office Action, dated Oct. 3, 2016, issued by the Mexican Patent Office in counterpart Mexican Patent Application No. MX/a/2014/000971.
Office Action, dated Oct. 5, 2016, issued by the State of Israel Ministry of Justice the Patent Office in counterpart Israeli Patent Application No. 230686.
Office Action dated Jan. 13, 2017, issued by the Russian Patent Office in corresponding Russian Application No. 2014107904.
Minushkina, L.O., et al., "Will valsartan become a first-rate medicine in the treatment of heart failure?", Farmateka No. 8(86), 2004, retrieved Jan. 29, 2016, retrieved from www.pharmateca.ru/archive/edition/1013, Total 30 pages (including English Translation).
Communication dated Jan. 11, 2017, issued by the Indonesian Patent Office in counterpart Indonesian application No. P00201400566.
Office Action dated Mar. 29, 2017 in corresponding Vietnamese Patent Application No. 1-2014-00317 with English translation.

* cited by examiner

1

LEFT VENTRICULAR DIASTOLIC FUNCTION IMPROVING AGENT

TECHNICAL FIELD

Present invention relates to an agent for improving left ventricular diastolic function, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof, and use thereof for treating heart failure and/or relieving a symptom, in particular use for treating diastolic heart failure and/or relieving a symptom.

BACKGROUND ART

Heart failure is a state, in which the pump function of a heart deteriorates due to various causes, and a blood volume corresponding to the demand for oxygen in peripheral major organs cannot be absolutely or relatively pumped, and a state, in which congestion is caused in lung or systemic venous system or in both systems and a disorder is caused in daily life. QOL of patients with heart failure is remarkably deteriorated due to the symptoms such as exertional dyspnea, shortness of breath, malaise, decrease in urine volume, limb edema and hepatomegaly.

It is estimated that there are currently more than a million patients with heart failure in this country, and the number is increasing for certain year by year due to the recent westernization of dietary habits and the aging society. Further, there are several million patients with heart failure each in the U.S. and in Europe, and the number is expected to further increase in the future. In addition, heart failure is known to be one of the diseases with poor prognoses. For example, it is reported that the patients with heart failure as a whole have a 50% chance of surviving five years and the patients with severe heart failure have a 30% chance of surviving three years, and heart failure shows the prognosis comparable to those of cancers. Thus, heart failure is placed as an extremely severe disease due to the large number of the patients and the poor prognosis.

In treating heart failure, the therapeutic strategy is generally decided depending on whether the pathological condition of the heart failure is chronic or acute.

So-called chronic heart failure, which refers to the chronic pathological change, is heart failure showing progressive exacerbation for a long time, and is known to be caused associated with for example myocardial disease or valvular disease. As the treatment of chronic heart failure, for example, an angiotensin-converting enzyme inhibitor, an angiotensin II receptor antagonist, a β-blocker, digitalis, a diuretic agent, an aldosterone antagonist or the like is administered.

On the other hand, so-called acute heart failure, which refers to the acute pathological change, is a state, in which the ventricular filling pressure increases because the compensation of the pump function of a heart rapidly falls down, and perfusion failure to main organs occurs thereby rapidly causing symptoms and signs based thereon. As the treatment of acute heart failure, a diuretic agent or a vasodilator for the intravenous administration is administered for removing the symptoms of congestion and dyspnea as soon as possible, and, when hypoperfusion is observed in particular, a cardiotonic agent such as dopamine or dobutamine is used.

As the pathological condition of heart failure, only systolic heart failure developing left ventricular systolic functional failure has been the focus of attention so far. However, heart failure, in which the left ventricular ejection fraction (LVEF, indication for the left ventricular systolic force) is normal or only slightly deteriorated, namely so-called diastolic heart failure, is recently regarded as problems.

Diastolic heart failure is known to be common among women and elderly people, in particular among patients with hypertension or diabetes. The anatomical characteristics of hearts of patients with diastolic heart failure are the concentric hypertrophy, and the ventricular wall thickens and the myocardial fibrillization is progressed, although there is no difference in the heart size in comparison with healthy individuals. As a result, the cardiac ventricle cannot dilate sufficiently during diastole and it constricts before the filling blood, and thus a sufficient blood volume cannot be pumped.

Patients with diastolic heart failure account for about a half of the whole heart failure patients. Although their prognoses are comparable to those of systolic heart failure patients, most therapeutic agents which are currently used for heart failure patients are agents, which have been clinically tested for systolic heart failure patients with lowered LVEF. There is no medicament, which has an effect to relieve diastolic functional failure and which has been proven to improve the prognoses of diastolic heart failure patients.

For the acute exacerbation phase of diastolic heart failure patients, a diuretic agent or a venodilatory vasodilator is used, as in the case of systolic heart failure patients. However, when such a medicament is administered to a patient with diastolic heart failure, there are problems in that the cardiac output and the blood pressure tend to decrease, or the patient is repeatedly hospitalized due to the higher frequency of recurrence in comparison with a systolic heart failure patient.

Further, it is said that most of the patients, who were diagnosed with systolic heart failure, actually suffer from left ventricular diastolic dysfunction.

Among the existing medicaments used for the treatment in the acute phase, there is no medicament which selectively relieves left ventricular diastolic dysfunction, and there are patients with symptoms of lung congestion or dyspnea, which are not relieved, or which need a long time to be improved. Thus, a new therapeutic agent is desired.

As described above, at this point, there is no effective therapeutic method for diastolic heart failure or left ventricular diastolic dysfunction, and thus the development of a new therapeutic means is urgently needed.

On the other hand, 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a prodrug thereof, or a cyclodextrin clathrate thereof is a selective agonist for EP4, which is a receptor subtype of prostaglandin E2, and is reported to be effective for immune diseases (autoimmune diseases such as amyotrophic lateral sclerosis, multiple sclerosis, Sjogren's syndrome, chronic rheumatoid arthritis and systemic lupus erythematosus, rejection after organ transplantation, and the like), asthma, neuronal cell death, arthritis, lung failure, pulmonary fibrosis, pulmonary emphysema, bronchitis, chronic obstructive pulmonary disease, liver damage, acute hepatitis, nephritis (acute nephritis and chronic nephritis), renal insufficiency, hypertension, myocardial ischemia, systemic inflammatory response syndrome, sepsis, hemophagocytic syndrome, macrophage activation syndrome, Still's disease, Kawasaki disease, burn, systemic granulomatosis, ulcerative colitis, Crohn's disease, hypercytokinemia at dialysis, multiple organ failure, shock, gastric ulcer, peptic ulcer such as duodenal ulcer, stomatitis, baldness, alopecia, loss in bone mass, sleep disorder, thrombosis, lower urinary tract symptom, hyperkalemia, neurodegenerative disease, and the like (please refer to Patent Documents 1, 2, 3 and 4).

Further, it is disclosed that a selective agonist for EP4 shows a renal vasodilation activity and thus is effective for renal insufficiency or renal dysfunction, or a state such as congestive heart failure caused by renal insufficiency or renal dysfunction (please refer to Patent Document 5).

On the other hand, it is also known that a compound having an EP4 antagonistic action acts therapeutically on heart failure (please refer to Patent Document 6).

As described above, there are conflicting findings as to whether EP4 works promotionally or inhibitory on the pathological condition of heart failure, and thus the situation was that there was no certain scientific findings. As a matter of course, there was no description or suggestion that 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a prodrug thereof, or a cyclodextrin clathrate thereof, which is an EP4 agonist, has an effect to improve left ventricular diastolic function, and acts therapeutically on heart failure patients, in particular diastolic heart failure patients.

PRIOR ART DOCUMENTS

Patent Documents

Patent Document 1: WO2003/009872
Patent Document 2: WO2006/016689
Patent Document 3: WO2006/016695
Patent Document 4: JP-A-2006-321737
Patent Document 5: JP-A-2001-233792
Patent Document 6: WO2002/016311

SUMMARY OF THE INVENTION

Problems that the Invention is to Solve

Diastolic heart failure is a disease caused by diastolic dysfunction of a heart, in particular of a left ventricle. Since there is currently no medicament showing an effect to improve left ventricular diastolic function itself, there is no effective medical therapy, which can preferentially treat diastolic heart failure so far.

For diastolic heart failure patients in the acute exacerbation phase, a diuretic agent or a vasodilator is sometimes prescribed with the purpose of relieving the symptoms of lung congestion and dyspnea. However, left ventricular diastolic dysfunction itself, which is the cause of the pathology thereof, is not cured, and the recurrence cannot be prevented.

Namely, an object of present invention is to provide a medicament, which improves diastolic function of a left ventricle itself without depending on the diuretic effect or vasodilation effect; controls the pathological condition of diastolic heart failure or left ventricular diastolic dysfunction; and prevents the recurrence, and can prevent dyspnea and death due to this pathological condition.

Means for Solving the Problems

EP4 agonists are generally predicted to relieve the congestion state of heart failure patients since EP4 agonists have a vasodilation effect and an effect to relieve renal dysfunction. However, these effects are the same as those of the existing vasodilators, and thus diastolic heart failure or left ventricular diastolic dysfunction is not relieved. Accordingly, when an EP4 agonist is administered to a patient with diastolic heart failure, there is a possibility that the agonist only causes the similar problems as those of a diuretic agent or a vasodilator, for example the decrease in the cardiac output, the decrease in the blood pressure, or the frequent recurrence.

As a result of extensive studies, the inventors of the present invention found that, among the compounds known as EP4 agonists, 4-[(2-{(2R)-2-[(1E,3S)-4-(4-fluorophenyl)-3-hydroxy-1-buten-1-yl]-5-oxo-1-pyrrolidinyl}ethyl)thio]butanoic acid (sometimes abbreviated to a compound A below) improves diastolic function of a left ventricle by directly acting on a heart, and can effectively treat particularly diastolic functional failure/diastolic dysfunction among heart failure types, and thus the inventors completed present invention.

Namely, present invention is as follows.

1. An agent for improving left ventricular diastolic function, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

2. The agent according to the above 1, which is an agent for treating heart failure and/or relieving a symptom.

3. The agent according to the above 2, wherein the heart failure is acute heart failure or chronic heart failure.

4. The agent according to the above 2 or 3, wherein the heart failure is diastolic heart failure.

5. The agent according to the above 2, wherein the symptom is congestion, dyspnea, shortness of breath, malaise, decrease in urine volume, limb edema and/or hepatomegaly.

6. The agent according to the above 1 to 5, which further has, an effect to improve left ventricular systolic function.

7. The agent according to the above 6, which is an agent for treating systolic heart failure and/or relieving a symptom.

8. The agent according to the above 7, wherein the symptom is congestion, dyspnea, shortness of breath, malaise, decrease in urine volume, limb edema and/or hepatomegaly.

9. An agent for improving the survival rate of heart failure, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

10. An agent for improving left ventricular distensibility, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

11. An agent for preventing myocardial fibrillization, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

12. A medicine for treating heart failure, which is produced by combining 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof, with one or more compounds selected from an angiotensin-converting enzyme inhibitor, an angiotensin II receptor antagonist, a β-blocker, a digitalis preparation, a diuretic agent, a natriuretic peptide, a vasodilator, a phosphodiesterase III inhibitor and/or an aldosterone antagonist.

13. An agent for treating diastolic heart failure and/or relieving a symptom, which includes a drug having an effect to improve left ventricular systolic function and an effect to improve left ventricular diastolic function, wherein the agent improves left ventricular diastolic function more selectively in comparison with left ventricular systolic function.

14. The agent according to the above 13, wherein the agent is 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

15. An agent for selectively improving left ventricular diastolic function, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof as an active ingredient, and which selectively improves left ventricular diastolic function in comparison with left ventricular systolic function.

16. The agent according to the above 15, which is an agent for treating diastolic heart failure and/or relieving a symptom.

17. An agent for treating heart failure, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof as an active ingredient, and which changes Peak positive dP/dt and Peak negative dP/dt of a mammal having a pathological condition of heart failure, wherein the change ratio of the Peak negative dP/dt calculated from the values before and after the administration of the agent is larger than the change ratio of the Peak positive dP/dt.

18. The agent according to the above 17, which is an agent for treating diastolic heart failure and/or relieving a symptom.

19. An agent for preventing heart failure associated with hypertension from occurring, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

20. An agent for treating diastolic heart failure and/or relieving a symptom, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

21. An agent for treating heart failure in which diastolic function is impaired, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof.

22. An agent for improving cardiac output, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or cyclodextrin thereof.

23. A method for improving left ventricular diastolic function, wherein 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal.

24. A method for treating heart failure and/or relieving a symptom, wherein 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal.

25. Use of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof for the manufacture of an agent for improving left ventricular diastolic function.

26. Use of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof for the manufacture of an agent for treating heart failure and/or relieving a symptom.

27. A compound of 4-[(2-{(2R)-2-[(1E,3S)-4-(4-fluorophenyl)-3-hydroxy-1-buten-1-yl]-5-oxo-1-pyrrolidinyl}ethy) thio]butanoic acid, a salt thereof, a solvate thereof or a cyclodextrin clathrate thereof for improving left ventricular diastolic function.

28. A compound of 4-[(2-{(2R)-2-[(1E,3S)-4-(4-fluorophenyl)-3-hydroxy-1-buten-1-yl]-5-oxo-1-pyrrolidinyl}ethy) thio]butanoic acid, a salt thereof, a solvate thereof or a cyclodextrin clathrate thereof for treating heart failure and/or relieving a symptom.

29. An agent for reducing the dose of an existing agent for treating heart failure, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or cyclodextrin thereof.

30. An agent for reducing the side effect of an existing agent for treating heart failure, which comprises 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or cyclodextrin thereof.

Effects of the Invention

Since 4-[(2-{(2R)-2-[(1E,3S)-4-(4-fluorophenyl)-3-hydroxy-1-buten-1-yl]-5-oxo-1-pyrrolidinyl}ethyl)thio]butanoic acid (the compound A), a salt thereof, a solvate thereof or a prodrug thereof, or a cyclodextrin clathrate thereof (sometimes abbreviated to "the compound used for the agent of present invention" below) has an effect to relieve diastolic dysfunction of a left ventricle by directly acting on a heart in addition to a vasodilation effect, it is effective particularly for diastolic heart failure among acute and chronic heart failure, and can relieve lung congestion, dyspnea, shortness of breath, malaise, decrease in urine volume, limb edema, hepatomegaly and/or the like more effectively than the existing vasodilators. Further, left ventricular diastolic function is generally impaired also in systolic heart failure, and the existing diuretic agents/vasodilators cannot relieve left ventricular diastolic dysfunction. Accordingly, it is expected that the compound used for the agent of present invention has better efficacy also for systolic heart failure in comparison with the existing diuretic agents/vasodilators.

MODE FOR CARRYING OUT THE INVENTION

Figure 1:
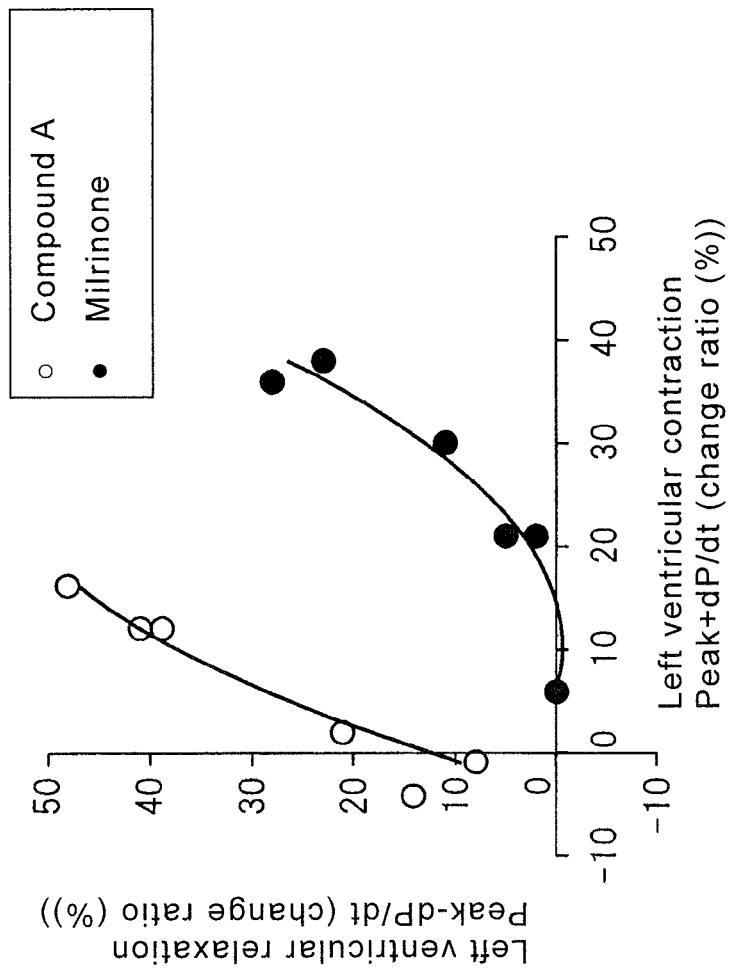
FIG. 1 shows the intensity balance of the left ventricular relaxation effects and the left ventricular contraction effects of the compound A and milrinone, which is an existing agent for treating heart failure, in an acute heart failure model.

The compound used for the agent of present invention improves diastolic function of a left ventricle, and can relieve the state, in which diastolic function of a left ventricle is impaired, namely left ventricular diastolic functional failure (which is sometimes called just diastolic functional failure).

In this specification, heart failure includes heart failure in the acute phase or in the chronic phase, namely acute heart failure or chronic heart failure. The definition of acute heart failure sometimes includes chronic heart failure in the acute exacerbation phase. Further, heart failure is sometimes called congestive heart failure.

Regarding heart failure, the dysfunction of a heart and the pathological conditions caused by the disorders are shown in Table 1 below. Diastolic heart failure (heart failure in diastole) is heart failure, in which only diastolic function of a left ventricle is impaired, but systolic function is normal or only slightly deteriorated. On the other hand, in systolic heart failure (heart failure in systole), both systolic function and diastolic function of a left ventricle are impaired. Diastolic heart failure and systolic heart failure are sometimes called diastolic failure and systolic failure, respectively. Further, the state, in which left ventricular diastolic function is impaired, is called left ventricular diastolic dysfunction, left ventricular diastolic functional failure, left ventricular diastolic disorder or left ventricular diastolic failure; and the state, in which systolic function is impaired, is also called left ventricular systolic dysfunction, left ventricular systolic functional failure, left ventricular systolic disorder or left ventricular systolic failure.

TABLE I

| | | Function | |
|---|---|---|---|
| | | Diastolic Function | Systolic Function |
| Pathological Condition | Diastolic Heart Failure (Diastolic Failure) | Impaired | Normal |
| | Systolic Heart Failure (Systolic Failure) | Impaired | Impaired |

Since the compound used for the agent of present invention improves diastolic function of a left ventricle and further reduces the afterload and the preload of a heart by causing arteriovenous relaxation, the compound is effective for systolic heart failure, in which both systolic function and diastolic function are impaired, as well as for diastolic heart failure, in which diastolic function is impaired.

The compound used for the agent of present invention, 4-[(2-{(2R)-2-[(1E,3S)-4-(4-fluorophenyl)-3-hydroxy-1-buten-1-yl]-5-oxo-1-pyrrolidinyl}ethy)thio]butanoic acid (which is sometimes called the "compound A" in this specification), namely the compound represented by the following formula,

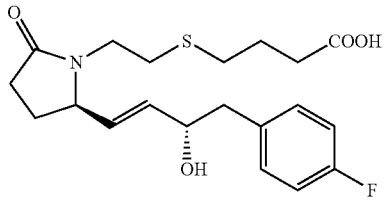 [SMILES: O=C(O)CCCSCCN1C(=O)CC[C@@H]1/C=C/[C@@H](O)Cc1ccc(F)cc1]

(in the formula,

⋰⋰⋰ represents a bonding at the other side of the plane of this page (namely, α-position), ▰ represents a bonding at this side of the plane of this page (namely, n-position) a salt thereof, a solvate thereof, a prodrug thereof or a cyclodextrin clathrate thereof is a compound disclosed in WO2003/009872.

The salt of the compound A includes all the pharmacologically acceptable salts. The pharmacologically acceptable salts are preferably low toxic water-soluble salts. The suitable salts include for example, salts of alkali metals (such as potassium, sodium and lithium), salts of alkaline earth metals (such as calcium and magnesium), ammonium salts (such as tetramethylammonium salt and tetrabutylammonium salt), salts of organic amines (such as triethylamine, methylamine, dimethylamine, cyclopentylamine, benzylamine, phenethylamine, piperidine, monoethanolamine, diethanolamine, tris(hydroxymethyl)methylamine, lysine, arginine and N-methyl-D-glucamine), acid addition salts (such as salts of inorganic acids (e.g. hydrochloride, hydrobromide, hydroiodide, sulfate, phosphate and nitrate), and salts of organic acids (e.g. acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate)).

The suitable solvates of the compound A include for example, solvates such as hydrates and solvates of alcohols (for example ethanol). It is preferable that the solvate is low toxic and water-soluble. Further, the solvate of the compound A also includes the solvates of salts of the compound A (such as salts of alkali (earth) metals, ammonium salts, salts of organic amines and acid addition salts).

As the prodrug of the compound A, for example, compounds, in which the carboxyl group of the compound A or a salt thereof is esterified or amidated, (for example, compounds in which the carboxyl group of the compound A is methyl-esterified, ethyl-esterified, propyl-esterified, butyl-esterified, phenyl-esterified, carboxymethyl-esterified, dimethylaminomethyl-esterified, pivaloyloxymethyl-esterified, 1-{(ethoxycarbonyl)oxy}ethyl-esterified, phthalidyl-esterified, (5-methyl-2-oxo-1,3-dioxolen-4-yl)methyl-esterified, 1-{[(cyclohexyloxy)carbonyl]oxy}ethyl-esterified or methyl-amidated) are mentioned.

The compound A, a salt thereof, a solvate thereof or a prodrug thereof may be converted into a corresponding cyclodextrin clathrate by the method described in the specification of JP-B-50-3362, JP-B-52-31404 or JP-B-61-52146 by using α-, β- or γ-cyclodextrin or a mixture thereof if necessary.

In this regard, a kind of any of the compound A, a salt thereof, a solvate thereof, a prodrug thereof and a cyclodextrin clathrate thereof may be used alone, or two or more kinds thereof may be used as a mixture.

[Preparation Method of the Compound Used for the Agent of Present Invention]

4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof, a prodrug thereof or a cyclodextrin clathrate thereof can be prepared by the known methods described above, for example the methods described in WO2003/009872, by combining the methods described in the specification of JP-B-50-3362, JP-B-52-31404 or JP-B-61-52146 if necessary.

[Toxicity]

Toxicity of the compound used for the agent of present invention is very low, and the compound is safe enough to be used as a medicine. For example, the compound A was not found to be toxic even when the dose reached 30 times as much as the dose, at which the vasodilation effect is observed with at least a single administration, in repeated oral administration to a dog for four weeks.

[Application to Pharmaceutical Preparations]

The compound used for the agent of present invention has an effect to improve diastolic function of a left ventricle, and thus is effective for heart failure (acute heart failure or chronic heart failure). The compound is effective particularly for heart failure in which the left ventricular ejection fraction is normal or only slightly deteriorated, namely diastolic heart failure among heart failure types. Diastolic heart failure is sometimes called diastolic failure. Furthermore, since the compound used for the agent of present invention improves diastolic function and systolic function of a left ventricle, and reduces the afterload and the preload of a heart by causing arteriovenous relaxation, the compound is effective for systolic heart failure, in which both systolic function and diastolic function are impaired, as well as for diastolic heart failure, in which diastolic function is impaired.

By administering the compound used for the agent of present invention to a patient with diastolic functional failure or systolic functional failure, the compound can relieve lung congestion, dyspnea, shortness of breath, malaise, decrease in urine volume, limb edema, hepatomegaly and/or the like associated with the pathological conditions.

In addition, as will be clarified in the following Examples, the compound used for the agent of present invention is also useful as an agent for improving the survival rate of heart failure, an agent for improving the left ventricular distensibility, and an agent for preventing the myocardial fibrillization. Furthermore, the compound used for the agent of present invention is also useful as an agent for improving QOL and an agent for improving the cardiac output.

Here, the improvement of the survival rate of heart failure means that the survival rate improves when the compound used for the agent of present invention is administered to a mammal (a human, a dog, a rat or the like) in which heart failure has been already developed, in comparison with the case without the administration. For example, it is said that the patients with heart failure as a whole have about 50% chance of surviving five years, and the five-year survival rate can be improved to about 60% or more, preferably about 70% or more, and further preferably about 80% or more when the agent of present invention is administered. Even when the survival rate is not improved, congestion, dyspnea, shortness of breath, malaise, decrease in urine volume, limb edema, hepatomegaly and/or the like are improved and thus QOL is also improved.

Here, the prevention of the myocardial fibrillization means that the progress of the myocardial fibrillization is prevented when the compound used for the agent of present invention is administered repetitively to a mammal (a human, a dog, a rat or the like) in which heart failure has been already developed, in comparison with the case without the administration. The prevention of the myocardial fibrillization leads to the prevention of the deterioration of the distensibility of a left ventricle (namely, passive diastolic disorder of a left ventricle) and thus left ventricular diastolic dysfunction is relieved.

Furthermore, as described above, in a patient with diastolic heart failure, the ventricle cannot dilate sufficiently during diastole and a sufficient blood volume cannot be pumped, due to the ventricular wall thickening and the myocardial fibrillization. Since the compound used for the agent of present invention prevents the myocardial fibrillization and prevents the deterioration of the distensibility in a left ventricle, the compound can be used as an agent for improving the cardiac output. It is possible to easily measure and decide whether the compound used for the agent of present invention has improved the cardiac output, by using an invasive, noninvasive or low-invasive device for monitoring the cardiac output.

In order to use the compound used for the agent of present invention with the above purpose, the compound used for the agent of present invention can be generally administered systemically or topically in the form of oral or parenteral administration after appropriately formulating the compound. As the parenteral administration, intravenous administration, intramuscular administration, subcutaneous administration, percutaneous administration and the like are mentioned. The administration path of the compound used for the agent of present invention may be any method as long as it is a method enabling the intravital administration of an effective amount thereof, and for example, oral administration or administration by injection, or administration as a patch is preferable.

Although the dose depends on the age, the weight, the symptom, the therapeutic effect, the administration method, the administration period and the like, the administration is generally oral and once to several times a day wherein an amount per each time is 0.1 ng to 1 mg per adult, parenteral and once to several times a day wherein an amount per each time is 0.1 ng to 1 mg per adult, or intravenous and continuous for 1 hour to 24 hours a day. For example, when the compound used for the agent of present invention is orally administered, it is preferable to administer the compound once to five times a day wherein an amount per each time is 100 ng to 10 μg per adult.

It goes without saying that the dose less than the above dose may be sufficient or the administration of the dose exceeding the above range may be necessary, because the dose varies under various conditions as described above.

Further, the compound used for the agent of present invention can be administered to a patient with heart failure after combining the compound with an existing agent for treating heart failure such as an angiotensin-converting enzyme inhibitor (such as enalapril, lisinopril, ramipril, captopril, benazepril, fosinopril, moexipril, perindopril, quinapril or trandolapril), an angiotensin II receptor antagonist (such as valsartan, candesartan, losartan, eprosartan, irbesartan or telmisartan), a sympathomimetic agent (such as dopamine or dobutamine), a β-blocker (such as carvedilol, bisoprolol or metoprolol), a digitalis preparation (such as digoxin or digitoxin), a diuretic agent (such as furosemide, bumetanide, triamterene, trichlormethiazide, azosemide, tolvaptan, ethacrynic acid or amiloride), a natriuretic peptide (such as carperitide or nesiritide), a vasodilator (such as nitroglycerin, isosorbide dinitrate, nicardipine, nicorandil or colforsin daropate), a phosphodiesterase III inhibitor (such as milrinone, aminophylline, pimobendan or olprinone), or an aldosterone antagonist (such as spironolactone or eplerenone). The compound used for the agent of present invention and the above agent for treating heart failure may be administered simultaneously by preparing a single pharmaceutical preparation including the both. Alternatively, the compound and the agent may be each formulated and administered individually or simultaneously.

By combining the compound used for the agent of present invention with an existing agent for treating heart failure, the dose of the existing agent for treating heart failure can be reduced, or the occurrence of an unfavorable phenomenon, which is generally called a side effect, can be prevented. Namely, the compound used for the agent of present invention is also useful as an agent for reducing the doses of the agents for treating heart failure cited above, or an agent for relieving the side effects.

As the means for producing a pharmaceutical preparation, when the compound used for the agent of present invention is administered, a solid agent for internal application and a liquid agent for internal application for oral administration, and injection for parenteral administration, an agent for external application, suppository, inhalant or the like are mentioned. The compound used for the agent of present invention can be made into a pharmaceutical preparation by a known method, for example, the method described in WO2003/009872.

The solid agent for internal application for oral administration includes a tablet, a pill, a capsule, a powder, granules and the like. The capsule includes a hard capsule and a soft capsule. Further, the tablet includes a sublingual tablet, an intraoral patch, an intraoral rapidly disintegrating tablet and the like.

In such a solid agent for internal application, the compound used for the agent of present invention is used as it is or after mixing with an excipient (such as lactose, mannitol, glucose, microcrystalline cellulose or starch), a binder (such as hydroxypropyl cellulose, polyvinyl pyrrolidone or magnesium metasilicoaluminate), a disintegrator (such as calcium fibrinoglycolate), a lubricant (such as magnesium stearate), a stabilizer, a solubilizing agent (such as glutamic acid or aspartic acid) and the like, followed by made into a pharmaceutical preparation by an ordinary method. Further, if it is necessary, the solid agent may be coated with a coating agent (such as white sugar, gelatin, hydroxypropyl cellulose or hydroxypropylmethyl cellulose phthalate), or may be coated with two or more layers. In addition, a capsule of an absorbable substance such as gelatin is also included.

The sublingual tablet is produced and prepared in accordance with a known method. For example, the compound used for the agent of present invention is mixed with an excipient (such as lactose, mannitol, glucose, microcrystal cellulose, colloidal silica or starch), a binder (such as hydroxypropyl cellulose, polyvinylpyrrolidone or magnesium metasilicate aluminate), a disintegrator (such as starch, L-hydroxypropyl cellulose, carboxymethyl cellulose, cross-carmellose sodium or calcium fibrinoglycolate), a lubricant (such as magnesium stearate), a swelling agent (such as hydroxypropyl cellulose, hydroxypropylmethyl cellulose, carbopole, carboxymethyl cellulose, polyvinyl alcohol, xanthan gum or guar gum), a swelling adjuvant (such as glucose, fructose, mannitol, xylitol, erythritol, maltose, trehalose, phosphate, citrate, silicate, glycine, glutamic acid or arginine), a stabilizer, a solubilizing agent (such as polyethylene glycol, propylene glycol, glutamic acid or aspartic acid), a flavor (such as orange, strawberry, mint, lemon or vanilla) and the like; made into a pharmaceutical preparation by an ordinary method; and used. Further, if it is necessary, the sublingual tablet may be coated with a coating agent (such as white sugar, gelatin, hydroxypropyl cellulose or hydroxypropylmethyl cellulose phthalate), or may be coated with two or more layers. In addition, an additive such as a preservative, an anti-oxidant, a coloring agent and a sweetener, which is generally used, may be added if necessary.

The intraoral patch tablet is produced and prepared in accordance with a known method. For example, the compound used for the agent of present invention is mixed with an excipient (such as lactose, mannitol, glucose, microcrystal cellulose, colloidal silica or starch), a binder (such as hydroxypropyl cellulose, polyvinylpyrrolidone or magnesium metasilicate aluminate), a disintegrator (such as starch, L-hydroxypropyl cellulose, carboxymethyl cellulose, cross-carmellose sodium or calcium fibrinoglycolate), a lubricant (such as magnesium stearate), an adhesive agent (such as hydroxypropyl cellulose, hydroxypropylmethyl cellulose, carbopole, carboxymethyl cellulose, polyvinyl alcohol, xanthan gum or guar gum), an adhesive adjuvant (such as glucose, fructose, mannitol, xylitol, erythritol, maltose, trehalose, phosphate, citrate, silicate, glycine, glutamic acid or arginine), a stabilizer, a solubilizing agent (such as polyethylene glycol, propylene glycol, glutamic acid or aspartic acid), a flavor (such as orange, strawberry, mint, lemon or vanilla) and the like; made into a pharmaceutical preparation by an ordinary method; and used. Further, if it is necessary, the intraoral patch tablet may be coated with a coating agent (such as white sugar, gelatin, hydroxypropyl cellulose or hydroxypropylmethyl cellulose phthalate), or may be coated with two or more layers. In addition, an additive such as a preservative, an anti-oxidant, a coloring agent and a sweetener, which is generally used, may be added if necessary.

The intraoral rapidly disintegrating tablet is produced and prepared in accordance with a known method. For example, the compound used for the agent of present invention is used as it is or as an active ingredient, in which bulk powder or granulation bulk powder particles are coated using an appropriate coating agent (such as ethyl cellulose, hydroxypropyl cellulose, hydroxypropylmethyl cellulose or acrylic acid methacrylate copolymer) and a plasticizer (such as polyethylene glycol or triethyl citrate), followed by mixing with an excipient (such as lactose, mannitol, glucose, microcrystal cellulose, colloidal silica or starch), a binder (such as hydroxypropyl cellulose, polyvinylpyrrolidone or magnesium metasilicate aluminate), a disintegrator (such as starch, L-hydroxypropyl cellulose, carboxymethyl cellulose, cross-carmellose sodium or calcium fibrinoglycolate), a lubricant (such as magnesium stearate), a dispersion adjuvant (such as glucose, fructose, mannitol, xylitol, erythritol, maltose, trehalose, phosphate, citrate, silicate, glycine, glutamic acid or arginine), a stabilizer, a solubilizing agent (such as polyethylene glycol, propylene glycol, glutamic acid or aspartic acid), a flavor (such as orange, strawberry, mint, lemon or vanilla) and the like to made into a pharmaceutical preparation by an ordinary method. Further, if it is necessary, the intraoral rapidly disintegrating tablet may be coated with a coating agent (such as white sugar, gelatin, hydroxypropyl cellulose or hydroxypropylmethyl cellulose phthalate), or may be coated with two or more layers. In addition, an additive such as a preservative, an anti-oxidant, a coloring agent and a sweetener, which is generally used, may be added if necessary.

The liquid agent for internal application for oral administration includes pharmaceutically acceptable water, suspension, emulsion, syrup, elixir and the like. In such a liquid agent, the compound used for the agent of present invention is dissolved, suspended, or emulsified in a generally used diluent (purified water, ethanol, a mixed liquid thereof or the like). Further, the liquid agent may further contain a humectant, a suspending agent, an emulsifying agent, a sweetener, a flavor agent, an aroma, a preservative, a buffer and the like.

The injection for parenteral administration includes a solid injection, which is used by dissolving or suspending in a solution, a suspension, an emulsion or time of use solvent. The injection is used by dissolving, suspending or emulsifying the compound used for the agent of present invention in a solvent. As the solvent, for example, distilled water for injection, physiological saline, vegetable oil, propylene glycol, polyethylene glycol, alcohol such as ethanol and a combination thereof are used. Further, this injection may include a stabilizer, a solubilizing agent (such as glutamic acid, aspartic acid or polysorbate 80 (registered trademark)), a suspending agent, an emulsifying agent, a soothing agent, a buffer, a preservative and the like. These are sterilized in the final process or produced and prepared by the aseptic manipulation. Further, an aseptic solid agent, for example a freeze-dried product, may be produced, and then used by dissolving in sterilizing or sterilized distilled water for injection or other solvents before use.

The patch is produced by a known or generally used formulation. For example, the patch is produced by melting the compound used for the agent of present invention in a base and flatting coating it on a support. The base for the patch is selected from known or generally used bases. For example, a kind selected from polymer bases (such as styrene-isoprene-styrene block copolymer, polyisobutylene rubber, acrylic ester resin, acrylic copolymer resin and silicone rubber), fat and oil, higher aliphatic acids, agents for accelerating transdermal penetration (such as oleic acid, isopropyl myristate, D-menthol or crotamiton), tackifiers (such as rosin derivative and alicyclic saturated hydrocarbon resin), agents for preventing irritation (such as glycerin and crotamiton) is used alone, or two or more kinds thereof are mixed and used. Further, a preservative, an anti-oxidant, a flavoring agent and the like may be included. As the patch, for example, plaster agents (such as matrix (such as adhesive single layer)-type patch and reservoir-type patch), cataplasms and the like are mentioned. The matrix-type patch further includes matrix-type patch of a drug-dispersing type, matrix-type patch of a drug-dissolving type and the like. The plaster agent is also called a tape agent.

EXAMPLES

Although present invention is explained in detail by Examples below, present invention is not limited to those Examples.

(1) Evaluation of Hemodynamics in Acute Heart Failure Model

<Preparation of Model Animal>

The acute heart failure model was produced by the following method. A male beagle (the weight was more than 10 kg) was anesthetized with pentobarbital sodium (30 mg/kg, intravenous administration), and then a tracheal catheter was introduced to the trachea and connected to a ventilator. The frequency of breath of the ventilator was set to 15 strokes per minute; the amount of ventilation was set to 20 mL/kg per stroke, and the respiration was controlled by using a mixed gas ($Air:O_2=3:0.2$ as an indication). The animal was fixed with the lateral position and the hair of the left chest area, left and right femoral areas and cervical region was cut. Pentobarbital sodium (5 mg/kg/hr) was intravenously administered continuously from right cephalic vein, and the anesthesia was continued. The chest was opened at the left fourth rib, and the ascending aorta origin was exfoliated. Lactated Ringer's solution was intravenously administered continuously from the catheter inserted to the left femoral vein (5 mL/min). Further, in order to prevent the arrhythmia from occurring, propranolol hydrochloride (0.3 mL/min) was administered continuously together with the volume overload (mixed with lactated Ringer's solution) until the completion of the experiment. The left anterior descending coronary artery (LAD) was ligated 30 minutes after the administration of lactated Ringer's solution. After the hemodynamics became stable, methoxamine hydrochloride was administered continuously from the left femoral vein. In order to increase the systemic vascular resistance and thus decrease the cardiac output, methoxamine hydrochloride was maintained at the volume of 5 to 10 μg/kg/min so that the cardiac output decreased by 20% or more in comparison with the cardiac output before the volume overload, and methoxamine hydrochloride was administered continuously until the completion of the experiment.

<Administration of Test Compounds>

From the point, at which the cardiac output decreased by 20% or more after the initiation of the continuous administration of methoxamine hydrochloride in comparison with the cardiac output before the administration of lactated Ringer's solution and other hemodynamics became stable, physiological saline (0.3 mL/min) was administered from the right femoral vein for 30 minutes (preceding phase of administration). Then, the compound A, (11α,13E,15α)-9-oxo-11,15-dihydroxy-16-(3-methoxymethylphenyl)-17,18, 19,20-tetranor-5-tiaprost-13-enoic acid methyl ester (the EP4 agonist described in Example 1 of WO2000/003980, abbreviated to a compound B below), and carperitide (atrial natriuretic peptide), nitroglycerin (a vasodilator), nicorandil (a vasodilator) and milrinone (a phosphodiesterase III inhibitor: a compound having a cardiac effect and a vasodilation effect), which are existing agents for treating heart failure, were each administered for 30 minutes with increasing the dose gradually from the right femoral vein at the doses in the following table. The administered groups (four examples each) and the doses are shown below.

TABLE 2

| Administered Group | Dose (administration with two increasing doses) |
|---|---|
| Vehicle | Physiological Saline |
| Compound A | 3, 10 ng/kg/min |
| Compound B | 3, 10 ng/kg/min |
| Carperitide | 0.3, 1 μg/kg/min |
| Nitroglycerin | 1, 3 μg/kg/min |
| Nicorandil | 10, 30 μg/kg/min |
| Milrinone | 1, 3 μg/kg/min |

The measurement of cardiac hemodynamics was conducted every 10 minutes both during the preceding phase of administration and during the continuous administration of each dose.

<Measurement of Hemodynamics>

Through the catheter introducer inserted to the right femoral artery, a pig tale catheter was introduced and indwelled in the left ventricle and connected to a disposable blood pressure transducer, and the left ventricular pressure (LVP) was measured through an amplifier for the measurement. Further, by using a hemodynamics analysis software, the left ventricular end-diastolic pressure (LVEDP: indication of preload), the systemic vascular resistance (SVR: indication of afterload), the cardiac output (CO), Peak positive dP/dt (Peak+dP/dt: indication of left ventricular systolic function), Peak negative dP/dt (Peak-dP/dt: indication of left ventricular diastolic function), the urine volume and the arterial oxygen pressure ($PaO_2$: indication of the blood oxygenation ability in the lung, and the decrease in the PaO₂ indicates the abnormality of the respiratory system, that is respiratory failure) were analyzed from the LVP waveform.

<Results>

The change ratios (%) of the Peak negative dP/dt 60 minutes after the administration of test compounds are shown in Table 3 below, and the change ratios (%) of the Peak negative dP/dt and the change ratios (%) of the Peak positive dP/dt of the compound A and milrinone are shown in FIG. 1.

TABLE 3

|  | Peak Negative dP/dt Change Ratio (%) |
|---|---|
| Compound A | 48 |
| Compound B | −3 |
| Carperitide | −6 |
| Nitroglycerin | −8 |
| Nicorandil | −7 |
| Milrinone | 23 |

As shown in Table 3, the compound A showed a stronger effect to improve left ventricular diastolic function in comparison with carperitide, nitroglycerin, nicorandil and milrinone, which are existing agents for treating heart failure. Further, the compound A increased the cardiac output by about 60%.

In addition, as shown in FIG. 1, the compound A showed a softer effect to improve systolic function (Peak+dP/dt change ratio=16%) in comparison with the effect to improve diastolic function. On the other hand, regarding milrinone that is an existing agent for treating heart failure, the effect to improve systolic function (Peak+dP/dt change ratio=38%) was stronger than the effect to improve diastolic function, and the cardiotonic action was superior. From the above results, it was considered that milrinone is not always appropriate for administering to a diastolic heart failure patient with normal systolic function because milrinone has a strong cardiotonic action, while the compound A selectively improves left ventricular diastolic function as compared with the effect to improve systolic function and thus is also effective for a diastolic heart failure patient with normal systolic function as well as a systolic heart failure patient in which both diastolic function and systolic function are impaired. In addition, although milrinone showed a strong left ventricular systolic effect also in a normal dog, the compound A did not show left ventricular diastolic action or left ventricular systolic action in a normal dog. Accordingly, the compound A had a remarkable effect showing pathologically specific left ventricular diastolic effect and left ventricular systolic effect. Furthermore, the compound A also improved the urine volume and the arterial oxygen pressure (the urine volume change ratio=145.4% and the PaO₂ change ratio=111.5%).

Further, as shown in Table 4 below, since the change ratios of the left ventricular end-diastolic pressures and the systemic vascular resistances of the compound A and the compound B known as an EP4 agonist are almost the same, the compound A and the compound B show similar vasodilation effects, but the compound B did not show the effect to improve diastolic function or the effect to improve systolic function (Peak+dP/dt change ratio=−4%; Peak-dP/dt change ratio=−3%).

TABLE 4

| Change Ratio (%) | Compound A | Compound B |
|---|---|---|
| Left Ventricular End-Diastolic Pressure | −42 | −41 |
| Systemic Vascular Resistance | −34 | −43 |
| Peak Positive dP/dt | 16 | −4 |
| Peak Negative dP/dt | 48 | −3 |

From the above results, it was shown that the compound used for the agent of present invention can be a useful agent for treating acute heart failure, since the compound has a strong effect to improve left ventricular diastolic function directly on a heart and also a soft effect to improve systolic function, which the existing EP4 agonists such as the compound B do not have. Further, it was indicated that the symptoms of decrease in urine volume, dyspnea and the like of acute heart failure can also be relieved.

(2) Comparison of Effects of Compound A and Structurally Similar Compounds in Acute Heart Failure Model In an experiment similar to that of (1) above, the effects to improve left ventricular diastolic function of the following EP4 agonists having similar structures to that of the compound A were evaluated.

Compound C: the compound described in Example 2 of JP-A-2001-181210 (dose: 3 µg/kg/min)

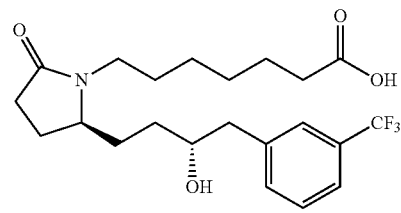 [SMILES: O=C(O)CCCCCCN1C(=O)CC[C@@H]1CC[C@@H](O)Cc1cccc(C(F)(F)F)c1]

Compound D: the compound described in Example 5 of WO2003/007941 (dose: 1 µg/kg/min)

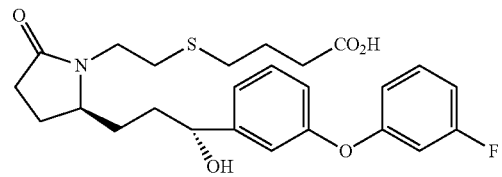 [SMILES: O=C(O)CCCSCCN1C(=O)CC[C@@H]1CC[C@@H](O)c1cccc(Oc2cccc(F)c2)c1]

The doses of the compounds C and D were the amounts showing vasodilation effects equivalent to that of the compound A.

<Results>

As shown in Table 5 below, the compound C and the compound D did not show an effect to improve diastolic function or an effect to improve systolic function, with the doses showing vasodilation effects almost equivalent to that of the compound A.

TABLE 5

| Change Ratio (%) | Compound C | Compound D |
|---|---|---|
| Left Ventricular End-Diastolic Pressure | −37 | −46 |

TABLE 5-continued

| Change Ratio (%) | Compound C | Compound D |
|---|---|---|
| Systemic Vascular Resistance | −14 | −42 |
| Peak Positive dP/dt | 2 | −9 |
| Peak Negative dP/dt | −1 | −5 |

From the above results, it was shown that the direct and strong effect to improve left ventricular diastolic function, which the compound used for the agent of present invention has, is a remarkable effect, which the compounds having similar structures as that of the compound A do not show.

(3) Measurement of Cardiac Function and Evaluation of Survival Rate Using Dahl Rat <Preparation of Model Animal>

A model of hypertensive heart failure, which is diastolic heart failure, was prepared by feeding solid feed for high salt load rat (corresponding to 8% salt) to 47-day-old male DIS/Eis rats (Dahl rats). Solid feed for normal feed rat (corresponding to 0.3% salt) was fed to a normal control group (10 examples).

<Administration of Test Compounds>

The test compounds were orally administered repeatedly for 90 days two times a day with the dose of 5 mL/kg using a stomach tube to 13-week-old Dahl rats. The dose of the compound A was 300 μg/kg and the dose of milrinone was 1000 μg/kg (30 examples each).

<Evaluation of Cardiac Function>

The cardiac functions were measured with using an ultrasound imaging device under 2% isoflurane anesthesia by a general anesthesia device for an animal before the administration (12 weeks old: grouping value), on the 45th day of the administration and the 91st day of the administration. The hair of the chest area of a rat was removed and the changes in the left ventricular end-diastolic dimension, the left ventricular end-systolic dimension, the end-diastolic left ventricular anterior wall thickness, the end-diastolic left ventricular posterior wall thickness, the end-systolic left ventricular posterior wall thickness and the left ventricular posterior epicardial surface were measured with placing a linear probe on the chest area with M-mode. Further, the left ventricular ejection fraction (LVEF) and the left ventricular diastolic wall strain (DWS) index as the indication of left ventricular diastolic function were calculated.

<Evaluation of Survival Rate>

The general state was observed once or twice a day throughout the experiment period, and dead or alive was confirmed and the general symptoms were recorded.

<Results>

Figure 2:
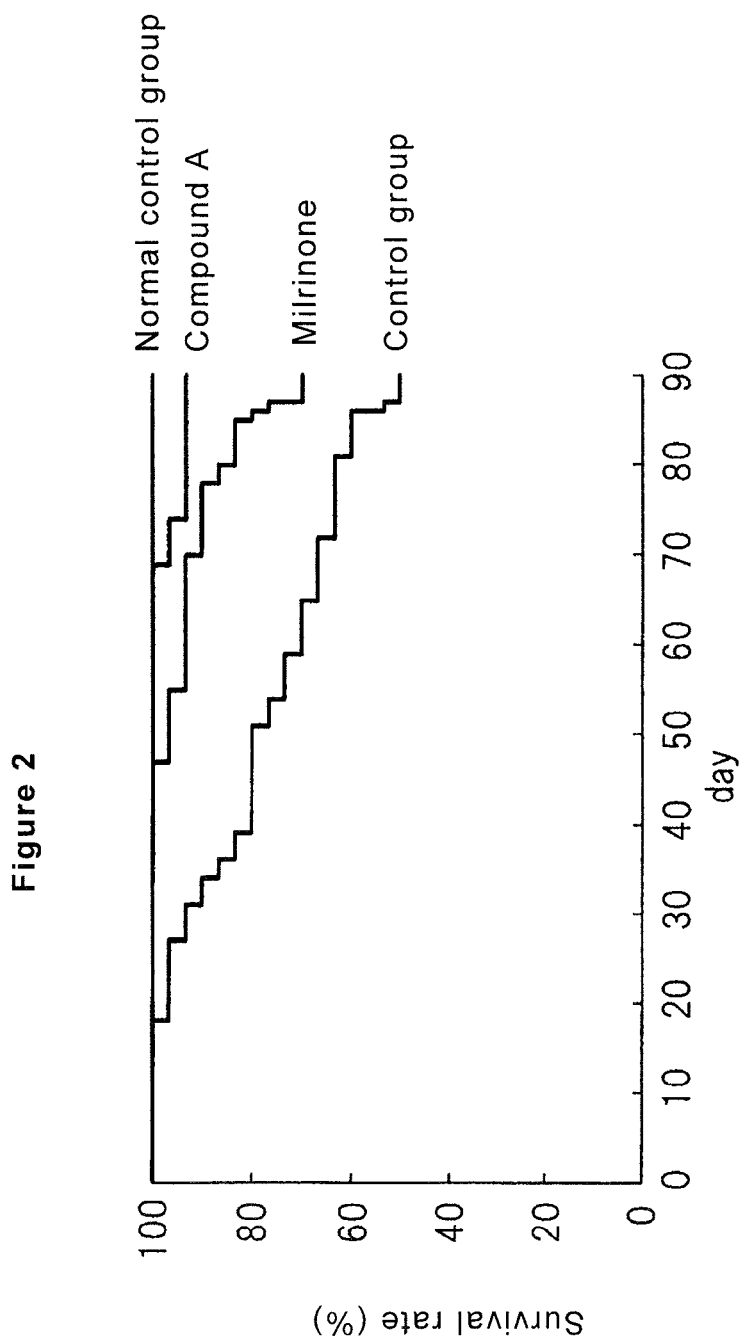
FIG. 2 shows the influences of the compound A and milrinone on the survival rate in a chronic heart failure model.
Figure 3:
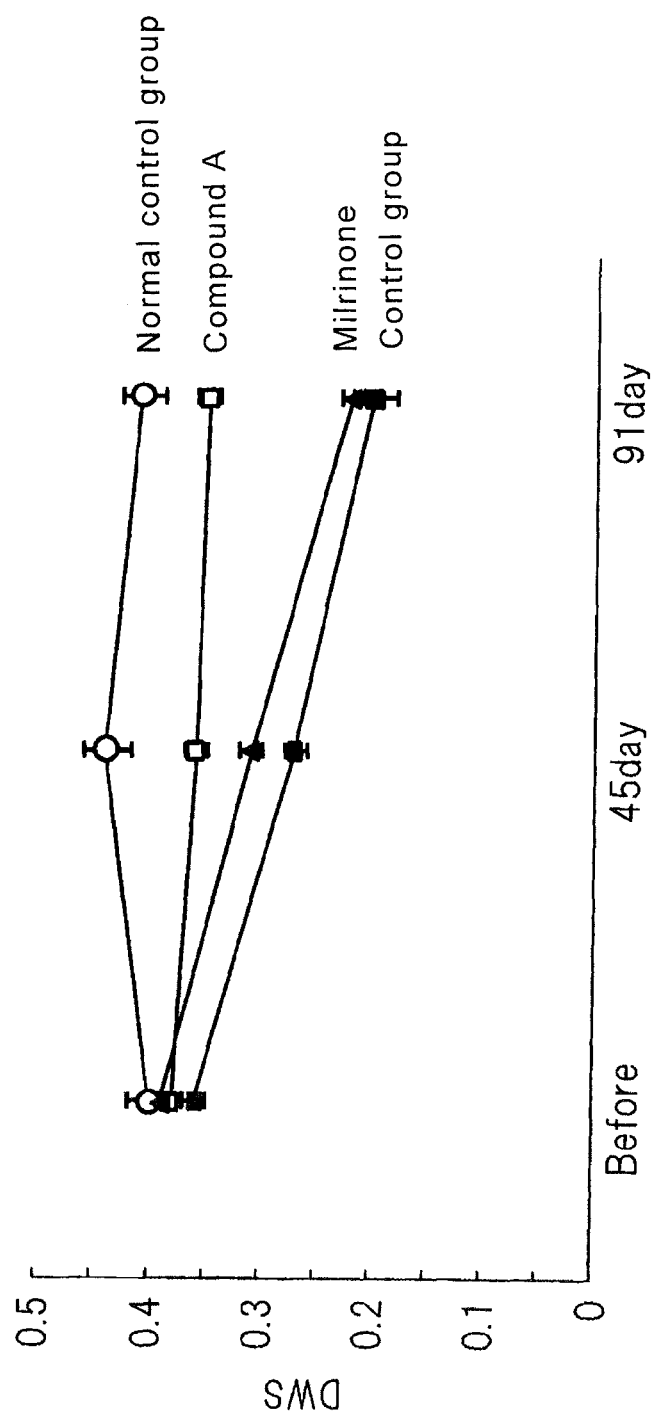
FIG. 3 shows the influences of the compound A and milrinone on the left ventricular diastolic wall strain (DWS) index in a chronic heart failure model.

The results are shown in FIGS. 2 and 3.

In the Dahl rat heart failure model, which is known as a chronic heart failure model, the compound A remarkably improved DWS. This means that the deterioration of the left ventricular distensibility by heart failure, that is, the myocardial fibrillization, was prevented, and left ventricular diastolic function was improved. Furthermore, the compound A drastically improved the survival rate.

On the other hand, milrinone which is an existing agent for treating heart failure did not improve DWS and the degree of the improvement of the survival rate was small as compared with that of the compound A.

From the above results, it was shown that the compound used for the agent of present invention has a strong effect to improve left ventricular diastolic function and improves the survival rate, and thus can be a useful agent for treating chronic heart failure.

In addition, since the prognosis of hypertensive heart failure was remarkably improved, it was shown that the compound used for the agent of present invention can be an agent for preventing heart failure associated with hypertension from occurring.

<Pharmaceutical Preparation Example>

Representative pharmaceutical preparation examples used in present invention are shown below.

Pharmaceutical Preparation Example 1: Tablet

According to an ordinary method, 4-[(2-{(2R)-2-[(1E,3S)-4-(4-fluorophenyl)-3-hydroxy-1-buten-1-yl]-5-oxo-1-pyrrolidinyl}ethyl)thio]butanoic acid (50 mg), magnesium stearate (10 g), carboxymethyl cellulose calcium (20 g) and microcrystalline cellulose (920 g) were mixed and made into a tablet to obtain 9000 tablets each including 5 μg of the active ingredient.

Pharmaceutical Preparation Example 2: Injection

In distilled water for injection (30 L), 4-[(2-{(2R)-2-[(1E,3S)-4-(4-fluorophenyl)-3-hydroxy-1-buten-1-yl]-5-oxo-1-pyrrolidinyl}ethyl)thio]butanoic acid (50 mg) and mannitol (1500 g) were dissolved, and the solution was sterilization-filtered with a membrane filter. Then, the solution was filled in 5 mL ampules for injection each in a volume of 3 mL to obtain injection (9000 ampules) including 5 μg of the active ingredient per ampule.

INDUSTRIAL APPLICABILITY

The compound used for the agent of present invention has an effect to improve diastolic function and an effect to improve systolic function in a left ventricle. Accordingly, the compound is effective for heart failure (acute heart failure or chronic heart failure), and is effective particularly for diastolic functional failure. Further the compound is also effective for symptoms such as congestion, dyspnea, shortness of breath, malaise, decrease in urine volume, limb edema and/or hepatomegaly associated with heart failure.

Therefore, by present invention, a new agent for treating heart failure that can relieve diastolic functional failure, for which no effective therapeutic method has been established, can be provided.

The invention claimed is:

1. A method for treating heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

2. The method according to claim 1, wherein the heart failure is acute heart failure or chronic heart failure.

3. The method according to claim 1, wherein the heart failure is diastolic heart failure.

4. The method of claim 1, wherein the method comprises improving left ventricular diastolic function.

5. The method of claim 4, wherein the heart failure is diastolic heart failure.

6. The method of claim 2, wherein the method comprises improving left ventricular diastolic function.

7. A method for treating heart failure by administering an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof to a mammal in need thereof, which changes Peak positive dP/dt and Peak negative dP/dt of a mammal having a pathological condition of heart failure, wherein the change ratio of the Peak negative dP/dt calculated from the values before and after the administration of the agent is larger than the change ratio of the Peak positive dP/dt.

8. The method according to claim 7, which is a method for treating diastolic heart failure.

9. A method for improving the survival rate of heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

10. A method for treating heart failure in which diastolic function is impaired, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

11. A method for reducing the dose of an existing agent for treating heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

12. A method for reducing the side effect of an existing agent for treating heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

13. The method according to claim 11 or 12, wherein the existing agent is one or more compounds selected from an angiotensin-converting enzyme inhibitor, an angiotensin II receptor antagonist, a β-blocker, a digitalis preparation, a diuretic agent, a natriuretic peptide, a vasodilator, a phosphodiesterase III inhibitor and/or an aldosterone antagonist.

14. A method for improving the survival rate of patients with heart failure associated with hypertension, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

15. A method for improving left ventricular diastolic function and/or treating systolic heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

16. A method for improving left ventricular diastolic function and/or improving left ventricular systolic function, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

17. A method for treating systolic heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

18. A method for improving left ventricular distensibility, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

19. A method for selectively improving left ventricular diastolic function, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof, which selectively improves left ventricular diastolic function in comparison with left ventricular systolic function.

20. A method for treating diastolic heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof, which selectively improves left ventricular diastolic function in comparison with left ventricular systolic function.

21. A method for treating and/or improving diastolic functional failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

22. A method for treating and/or improving diastolic functional disorderdysfunction, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

23. A method for treating diastolic heart failure, wherein an effective amount of 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal in need thereof.

24. The method according to claim 16, which is a method for improving left ventricular diastolic function and for improving left ventricular systolic function.

25. The method of claim 16, which is a method for improving left ventricular diastolic function.

26. A method for treating and/or relieving dyspnea associated with heart failure, wherein 4-[(2-{(2R)-2-[(1E,3S)-4-(4-fluorophenyl)-3-hydroxy-1-buten-1-yl]-5-oxo-1-pyrrolidinyl}ethyl)thio]butanoic acid, a salt thereof, a solvate thereof or a cyclodextrin clathrate thereof is administered to a mammal.

* * * * *

UNITED STATES PATENT AND TRADEMARK OFFICE
CERTIFICATE OF CORRECTION

| | |
|---|---|
| PATENT NO. | : 9,682,065 B2 |
| APPLICATION NO. | : 14/236474 |
| DATED | : June 20, 2017 |
| INVENTOR(S) | : Toshiya Kanaji, Kazuhiro Fuchibe and Masaya Takahashi |

Page 1 of 1

It is certified that error appears in the above-identified patent and that said Letters Patent is hereby corrected as shown below:

In the Claims

Column 20, Lines 34-35: In Claim 22, delete "diastolic functional disorderdysfunction" and insert --diastolic dysfunction--

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*